United States Patent [19]

Callingham et al.

[11] Patent Number: 5,028,411

[45] Date of Patent: * Jul. 2, 1991

[54] PHARMACEUTICAL COMPOSITIONS

[75] Inventors: Brian A. Callingham, Cambridge; Robert C. Hider, Clacton; George Kontoghiorghes, London; Michael A. Stockham, Saffron Walden, all of England

[73] Assignee: National Research Development Corporation, London, England

[*] Notice: The portion of the term of this patent subsequent to Mar. 11, 2003 has been disclaimed.

[21] Appl. No.: 318,513

[22] Filed: Mar. 2, 1989

Related U.S. Application Data

[63] Continuation of Ser. No. 63,764, Jun. 23, 1987, abandoned, which is a continuation of Ser. No. 723,280, Apr. 15, 1985, abandoned.

[30] Foreign Application Priority Data

Apr. 19, 1984 [GB] United Kingdom ................. 8410290

[51] Int. Cl.$^5$ ......................... A61K 9/04; A61K 9/68; A61K 31/555
[52] U.S. Cl. ....................................... 424/45; 424/48; 424/647; 514/184; 514/502
[58] Field of Search ........................... 424/45, 48, 147; 514/184, 502

[56] References Cited

U.S. PATENT DOCUMENTS

| | | | |
|---|---|---|---|
| 2,865,938 | 12/1958 | Rosenfelder | 260/439 |
| 2,904,573 | 9/1959 | Oroshnik et al. | 260/439 |
| 3,130,204 | 4/1964 | Tate et al. | 260/345.9 |
| 3,338,718 | 8/1967 | Olson | 260/345.9 |
| 3,376,317 | 4/1968 | Stephens et al. | 260/345.9 |
| 3,821,192 | 6/1974 | Montgomery et al. | 260/209 R |
| 4,018,907 | 4/1977 | Scarpellino | 424/250 |
| 4,018,934 | 4/1977 | Parliment | 426/250 |
| 4,058,621 | 11/1977 | Hill | 424/295 |
| 4,311,691 | 1/1982 | Fichera | 424/48 |
| 4,315,942 | 2/1982 | Corden | 514/502 |
| 4,575,502 | 3/1986 | Hilder et al. | 514/184 |

FOREIGN PATENT DOCUMENTS

| | | |
|---|---|---|
| 0094149 | 11/1983 | European Pat. Off. |
| 0107458 | 5/1984 | European Pat. Off. |
| 2613500 | 10/1976 | Fed. Rep. of Germany |
| 2130M | 11/1963 | France |
| 1377006 | 12/1974 | United Kingdom |
| 2128998 | 5/1984 | United Kingdom |

OTHER PUBLICATIONS

*European Search Report:* re: (Corresponding European Patent Applications-EPA 94,194; EPA 107,458; and *Chem. Abstracts*, vol. 75, No. 18 (Nov. 1, 1971)).
*United Kingdom Search Report:* re: (Corresponding U.K. Patent Application-GB 2128998 [equivalent of U.S. Ser. No. 542,976, already cited]).
Weatherall et al (Eds.), Oxford Textbook Medicine, Oxford University Press, 1983, vol. 1, p. 7.7.
Martindale, The Extra Pharmacopoeia, The Pharmaceutical Press, 1973, pp. 81 and 739.
Tate et al., U.S. application Ser. No. 314,141 filed 09/19/63.
Kimura et al, Chem. Pharm. Bull. (1980), 28, 2570–2579, "Central Depressant Effects of Maltol Analogs in Mice".
Pitt and Gupta (1975), pp. 137–173, Proceedings of a Symposium, "Development of Iron Chelators for Clinical Use", Anderson & Miller (Eds.), Pfizer Technical Bulletin, 04/A/Mar. 1974.
Pfizer, Technical Bulletin No. 865 and No. 867, Data Sheet.

(List continued on next page.)

*Primary Examiner*—Frederick E. Waddell
*Attorney, Agent, or Firm*—Nixon & Vanderhye

[57] ABSTRACT

Pharmaceutical compositions for the buccal or nasal administration of a neutral 3:1 hydroxypyrone:iron(III) complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms are of value for the treatment of iron deficiency anaemia.

36 Claims, 6 Drawing Sheets

PHARMACEUTICAL COMPOSITIONS

This application is a continuation of application Ser. No. 07/063,764 filed on June 23, 1987, now abandoned, which is a continuation of Ser. No. 723,280, filed Apr. 15, 1985 also now abandoned.

This invention relates to pharmaceutical compositions containing iron compounds for the treatment of iron deficiency anaemia.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency amaemia is commonly encountered in pregnancy and may also present a problem in the newly born, particularly in certain animal species such as the pig. Moreover, in certain pathological conditions there is a mal distribution of body iron leading to a state of chronic anaemia. This is seen in chronic diseases such as rheumatoid arthritis, certain haemolytic diseases and cancer.

Although a wide range or iron compounds is already marketed for the treatment of iron deficiency anaemia, the level of iron uptake by the body from these compounds is often quite low thereby necessitating the administration of relatively high dosage levels of the compound. The administration of high dose, poorly absorbed, iron complexes may cause siderosis of the gut wall and a variety of side effects such as nausea, vomiting, constipation and heavy malodorous stools.

In UK patent application No. 8327612, published as GB 2128998A, and corresponding applications including Canadian application No. 446932 and U.S. application Nos. 542976 and 601485, a group of iron complexes is described which have been identified as being of particular value for use at relatively low dosage levels in the treatment of iron deficiency anaemia. It is an object of the present invention to provide an alternative method of formulating these iron compounds having certain advantages over the methods described in this previous application.

Accordingly the present invention comprises a pharmaceutical composition for the buccal or nasal administration of a neutral 3:1 hydroxypyrone:iron(III) complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms.

The iron complexes present in the pharmaceutical compositions according to the present invention contain iron in the ferric state and are netural, i.e. there being an internal balance of charges between the ferric cation and the three anions derived from the hydroxypyrone (through the conversion OH→O⁻). The iron complexes of use in the present invention are thus of the 3:1 form, as opposed to complexes of the 2:1 and 1:1 forms which instead contain a 2:1 or 1:1 molar proportion of hydroxypyrone anion:iron(III) and require the presence of an additional non-covalently bound anion or anions, such as chloride, to balance the charge on the ferric cation.

The substituted 3-hydroxy-4-pyrones may carry more than one type of aliphatic hydrocarbon group but this is not usual and, indeed, substitution of two rather than three, and particularly by only one aliphatic hydrocarbon group is preferred. The aliphatic hydrocarbon groups may be cyclic or acyclic, having a branched chain or especially a straight chain in the latter case, and may be unsaturated or especially saturated. Groups of from 1 to 4 carbon atoms and particularly of 1 to 3 carbon atoms are of most interest. Alkyl groups are preferred, for example cyclic groups such as cyclopropyl and especially cyclohexyl but, more particularly preferred are acyclic alkyl groups such as n-propyl and isopropyl, and especially ethyl and methyl. Substitution at the 2- or 6-position is of especial interest although, when the ring is substituted by the larger aliphatic hydrocarbon groups, there may be an advantage in avoiding substitution on a carbon atom alpha to the

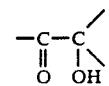

system. This system is involved in the complexing with iron and the close proximity of one of the larger aliphatic hydrocarbon groups may lead to steric effects which inhibit complex formation.

Preferred hydroxypyrones of use in complexes according to the present invention have the formula (I), with specific hydroxypyrones of particular interest having the formulae (II) and (III):

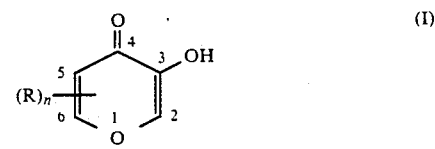

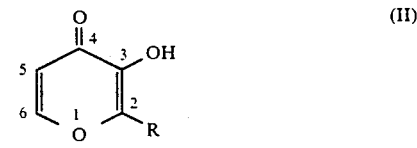

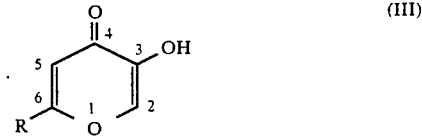

in which R is an alkyl group, for example methyl, ethyl, n-propyl isopropyl or butyl, and n is 0, 1, 2 or 3 (the ring being unsubstituted by any alkyl group when n is 0). Among these compounds 3-hydroxy-2-methyl-4-pyrone (maltol; II, R=CH$_3$) is of most interest, whilst 3-hydroxy-4-pyrone (pyromeconic acid; I, n=0) 3-hydroxy-6-methyl-4-pyrone (isomaltol; III, R=CH$_3$) and particularly 2-ethyl-3-hydroxy-4-pyrone (ethylpyromeconic acid; II, R=C$_2$H$_5$) are also of especial interest.

In the case of certain of the hydroxypyrones referred to above, for example maltol, ethypyromeconic acid and isomaltol, the formation of an iron complex of the compound has been referred to in the literature, although it should be noted that the procedures described in the literature for the production of such complexes often would not provide complexes of the 3:1 form which are used in the pharmaceutical compositions according to the present invention.

The iron complexes are conveniently prepared by the reaction of the hydroxypyrone and iron ions, the latter conveniently being derived from an iron salt, particularly a ferric halide and especially ferric chloride. The reaction is conveniently effected in a suitable mutual solvent and water may often be used for this purpose. If desired, however, an aqueous/organic solvent mixture may be used or an organic solvent, for example ethanol, methanol or chloroform and mixtures of these solvents together and/or with water where appropriate. In particular, methanol or especially ethanol may be used where it is desired to effect the separation of at least a major part of a by-product such as sodium chloride by precipitation whilst the iron complex is retained in solution.

It should be appreciated that the nature of the iron complex obtained by the reaction of a hydroxypyrone and iron ions will depend both on the proportion of these two reactants and upon the pH of the reaction medium. Thus, for the preparation of the 3:1 ferric complex, the hydropyrone and the ferric salt are conveniently mixed in solution in a 3:1 molar proportion and the pH adjusted to a value in the range of 6 to 9, for example 7 or 8. If a similar excess of hydroxypyrone:iron is employed but no adjustment is made of the acidic pH which results on the admixture of the hydroxypyrone and an iron salt such as ferric chloride, then a mixture of the 2:1 and 1:1 complex will instead be obtained. Adjustment of the pH may conveniently be effected by the addition of solid sodium carbonate. However, a possible alternative, which is of particular interest when preparing the iron complexes in batches of 20 g or more, is to use a hydroxide base such as sodium or ammonium hydroxide. When using a hydroxide base, the reaction may conveniently be carried out in 4:1 v/v ethanol:water as a solvent and the pH adjusted by the addition of a 2 molar aqueous solution of the base. It will be appreciated that the presence of a proportion of water in the reaction mixture will lead to the retention of a by-product in the iron complex on evaporation of the solvent (a chloride where the iron salt is ferric chloride). However, this can be removed, if desired, by procedures such as crystallisation from a suitable solvent system or sublimation in the particular case of ammonium chloride.

Reaction to form the iron complex is generally rapid and will usually have proceeded substantially to completion after 5 minutes at about 20° C., although a longer reaction time may be used if necessary. Following separation of any precipitated by-product, such as sodium chloride in the case of certain solvent systems, the reaction mixture may conveniently be evaporated on a rotary evaporator or freeze dried to yield the solid iron complex. This may, if desired, by crystallised from a suitable solvent, for example water, an alcohol such as ethanol, or a solvent mixture, including mixtures containing an ether.

Whilst for some uses it may be appropriate to prepare the iron complex in substantially pure form, i.e. substantially free from by-products of manufacture, in other cases, for example with a solid oral formulation as described hereinafter, the presence of by-products such as sodium chloride may be quite acceptable. In general, however, the neutral 3:1 hydroxypyrone:iron(III) complex is of particular interest in a form which is substantially free at least from those by-products which are complexes containing different proportions of hydroxypyrone and iron, in particular the 2:1 and 1:1 complexes.

The term "substantially free from" is used herein to indicate the presence of 10% by weight or less of the material referred to.

As indicated hereinafter, it may be advantageous under some circumstances for the iron complex to be used in admixture with the free pyrone. It is possible to produce such a mixture by mixing the two components either in the solid form or in solution, followed by isolation of a solid mixture in the latter case when a solid composition is required. However, it may be more convenient to obtain such a mixture by reacting a molar proportion of the pyrone and iron ions of greater than 3:1. It should be stressed, however, that the conditions as well as the proportion of reactants used in the reaction are of importance if a mixture of the free pyrone and the preferred neutral 3:1 complex is to be obtained. In particular, as indicated previously, the pH of the reaction mixture is particularly important and, because of this fact, certain prior art procedures concerned with the use of iron pyrone complexes in food colouring, for example as described in U.S. Pat. No. 4,018,907, substantially fail to yield the 3:1 complex even though an excess of the pyrone is present, owing to the lack of pH control.

Certain hydroxypyrones, such as maltol, are available commercially. With others, a convenient starting material in many instances consists of pyromeconic acid which is readily obtainable by the decarboxylation of meconic acid. Thus, for example, pyromeconic acid may be reacted with an aldehyde to insert a 1-hydroxyalkyl group at the 2-position, which group may then be reduced to produce a 2-alkyl-3-hydroxy-4-pyrone. The preparation of 2-ethyl-3-hydroxy-4-pyrone, etc., by this route is described in U.S. application Ser. No. 310,141 (series of 1960).

It will be appreciated that these are not the only routes available to these compounds and their iron complexes and that various alternatives may be used as will be apparent to those skilled in the art.

The iron complexes described herein have been found to be particularly suited to the treatment of iron deficiency anaemia, both in humans and also in a veterinary context and particularly for the treatment of various mammalian species, especially pigs. The pharmaceutical compositions of the present invention are, however, most especially suited to human use. The chelating agents which the iron complexes contain, and particularly maltol, have a high affinity for iron ($\log \beta_3 = 30$ for maltol) but a lower affinity for copper (II), zinc (II), calcium and magnesium. Both the high affinity of maltol for iron and its low affinity for calcium are reflected in its $K_{sol}$ value {$\log K_{sol}$ is defined as being equal to $\log \beta_{Fe(L)n} + 21 - [pK_{sp} + n \log a_L(H^+) + m \log a_L(Ca^{++})]$ where $\log \beta_{Fe(L)n}$ is the cumulative affinity constant of the ligand in question for iron(III), $pK_{sp}$ is the negative logarithm of the solubility product for $Fe(OH)_3$ and has a value of 39, n and m are the number of hydrogen and calcium ions, respectively, which are bound to the ligand, and $a_L(H^+)$ and $a_L(Ca^{++})$ are the affinities of the ligand for hydrogen ions and calcium ions, respectively}. In order to solubilise iron(III) hydroxide, $\log K_{sol}$ must be greater than 0. The value of $K_{sol}$ for maltol is 8.0 and this is also sufficiently large to prevent appreciable competition from phytate, phosphate, thiols and other potential ligands likely to occur in the intestinal lumen. In order to exchange iron efficiently with transferrin, the $\log K_{sol}$ value should be close to that of apotransferrin, which is 6.0, so that maltol is also suitable in this respect. Moreover, although the neutral 3:1 maltol:iron(III) complex is thermodynamically stable (thermodynamic stability constant=30) it is also extremely labile and is therefore able to donate iron to high affinity sites, such as those found in apotransferrin. The half life for the exchange of iron(III) between the maltol complex and apotransferrin is 1 minute whereas, by contrast, the corresponding figure for the 3:1 complex of EDTA with iron(III) is 4 days.

It will be appreciated, however, that in addition to possessing properties such as those described above for iron maltol, a compound which is to act as a source of iron through oral administration is required to to show a high level of membrane permeability. An indication of the properties of a compound in this respect is provided by the value of the partition coefficient ($K_{part}$) obtained on partition between n-octanol and Tris hydrochloride (20 mM, pH 7.4; Tris representing 2-amino-2-hydroxymethylpropane 1,3-diol) at 20° C. and expressed as the ratio (concentration of compound in organic phase)/(concentration of compound in aqueous phase). The value of $K_{part}$ for the neutral 3:1 maltol:iron(III) complex is 0.5, which is well placed in the preferred range of 0.2 to 1.0 and compares favourably with the figures of 0.001 and 0.0015 for the EDTA:iron(III) complex and iron(III) ascorbate, respectively.

The value of the iron complexes used in the present invention is confirmed by various in vitro and in vivo tests. Thus, their ability to permeate biological membranes is confirmed in practice by tests of the ability of the $^{59}Fe$ labelled iron complexes to permeate erythrocytes. Moreover, iron complexes of the present invention have been found to exhibit a high level of efficiency in promoting iron uptake, as measured in the rate small intestine, as compared with a range of other iron complexes currently marketed for the treatment of iron deficiency anaemia. In vivo experiments in the cat and rat have confirmed the value of iron maltol compounds as a source of iron, the iron uptake obtained either on intravenous administration or on direct administration into the small intestine being markedly superior to that obtained with commercially available iron compounds such as iron sulphate, iron EDTA and iron gluconate. It was found from these experiments that the iron was not excreted to any significant extent in the urine but became generally distributed throughout the body, the complexes donating iron to transferrin to an equilibrium level once they are present in the bloodstream.

The neutral 3:1 hydroxypyrone ferric complexes are of particular interest in the treatment of iron deficiency anaemia, rather than the 2:1 and 1:1 complexes. However, as reported in UK patent application GB 2128998A, although these 3:1 complexes are stable over a wide pH range from about 4 or 5 up to 10, they will dissociate at the pH values of less than 4 prevailing in the stomach to form a mixture of the 2:1 and 1:1 complex together with the free hydroxypyrone, and it has been found that the blood levels of $^{59}Fe$ achieved on administration of the 3:1 complex into the small intestine are much higher than when administration is made into the stomach. However, when the stomach contents is flushed to the small intestine in in vivo cat experiments an increase of iron uptake occurs almost immediately. Several methods of overcoming the undesirable effects of this dissociation on iron uptake have been proposed in UK Patent Application GB 2128998A but the present invention involves another, quite different approach which is not described therein and which is of particular value.

It has been found that formulation of the iron complexes described herein as a pharmaceutical composition adapted for buccal or nasal administration has a number of advantages. Firstly, since the buccal and nasal cavities represent an environment with a pH in the region of 7, a 3:1 neutral iron(III) complex will be taken up by the membranes of the buccal cavity (including the tongue) and the nasal passages in the neutral form, without any significant degree of disproportionation to the corresponding 2:1 and 1:1 complexes. Such a form of administration thus often provides a simpler alternative to the use of pharmaceutical compositions of the type described in UK Patent Application GB 2128998A which are intended to protect the 3:1 neutral iron(III) complex from the strongly acid environment of the stomach. Buccal or nasal administration is applicable to the iron complexes of the present invention in view of the acceptable taste thereof, particularly as compared with the very bitter taste of many of the existing commercial preparations for the treatment of iron deficiency anaemia.

A second advantage of the compositions according to the present invention is that they provide some form of safety measure as regards overdoses, for example those arising from the taking by children of medication prescribed for adults in the same household. This can pose a considerable problem with existing iron preparations and, although the present iron complexes in any case generally have the advantage of lower toxicity and lower unit dosage levels, the compositions of the present invention provide an added advantage. Thus, it is difficult rapidly to ingest a large quantity of the iron complex from the buccal cavity or nasal passages and overdosage problems are more likely to arise through swallowing the medicament. If this is done, however, and the iron complex is not formulated in such a way as to protect it from the acid environment of the stomach, disproportionation to the 2:1 and 1:1 complexes will occur which has the effect of reducing the level of iron uptake from the overdose. The lower toxicity of the iron complexes of the present invention will avoid much of the local damage to the gastrointestinal tract which can occur in such circumstances with many commercial iron preparations.

It will be seen, therefore, that the method of formulation described herein has certain significant advantages in the particular context of the present iron complexes.

In formulating the iron complexes in the form of a pharmaceutical composition according to the present invention they may conveniently be combined with a physiologically acceptable diluent or carrier adapted to buccal or nasal administration. Such diluents and carriers may include various materials in current use in compositions for buccal or nasal administration. Buccal administration is of particular interest and in this case a solid composition is preferred. Such compositions adapted for retention in the mouth rather than swallowing, and consequent release of the active component in the buccal cavity, may take very many forms. These include chewing or bubble gum, lollipops, boiled sweets, effervescent tablets and particularly pastilles and lozenges. Most usually, therefore, the composition will be chewed or sucked to lead to release of the iron complex in the mouth, although it is possible to use tablets, for example in the form of a disc of polymeric material, which are attached to the wall of the buccal cavity and which gradually release the iron complex without being sucked. If desired, liquid compositions may be used in the buccal cavity, particularly aerosol sprays, but these are of less interest. All of these forms of compositions are taken through the mouth but, in contrast to the oral compositions described in the earlier patent application, are adapted to release of the iron complex in the mouth rather than on being swallowed (although in the process of chewing, sucking etc. a proportion of the iron complex may of course pass into the stomach). Preferred forms of compositions are pastilles and lozenges and such compositions are sometimes described by the term "linguet", this being a composition suitable for sub-lingual use.

Specific carriers which may be used in pastilles and lozenges are described in various tests including the British Pharmacoepia, the British Pharmacoepia Codex and Martindale, the Extra Pharmacopoeia. One particular example of a base for pastilles is described in the 1980 British Pharmacoepia and consists of a mixture of gelatin, glycerine, sugar, citric acid and amaranth. The rate at which the pastille dissolves in the mouth may be varied as desired with a view to achieving a good level of uptake of iron, the rate of dissolution being reduced, for example, by increasing the proportion of gelatin used. Pastilles may conveniently be prepared by forming a melt containing a suitable amount of the iron complex and the carrier and then pouring this into a mould and allowing to dry. One particular example of a base for lozenges is described in the 1959 British Pharmacoepia Codex and consists of a mixture of sucrose, acacia and rose oil water. Once again, the rate of dissolution may be controlled by variation of the ingredients in the base material. Lozenges may conveniently be prepared either by forming a "dough" from which the lozenges are cut or, preferably, by compression. If desired, further flavourings can be incorporated in the pastilles or lozenges but the taste of the iron complexes is so acceptable that this may be unnecessary, except perhaps for paediatric formulations.

Where compositions for nasal administration are employed these will usually be liquid and may comprise water and/or suitable organic solvents. Such compositions may conveniently be used either as drops or in the form of an aerosol spray. It is, however, possible to use solid compositions in the form of a snuff if so desired. In the case of compositions for nasal administration, the physical characteristics of the compositions may not differ so markedly from those of compositions for other modes of administration as in the case with compositions for buccal administration. However, the intended mode of all forms of compositions according to the present invention will in general be clear from the packaging of the composition, for example in a container for the dispersing of a spray or drops, and/or the instructions provided therewith specifying buccal or nasal usage.

The compositions according to the present invention may be formulated in unit dosage form, i.e. in the form of discrete portions containing a unit dose, or a multiple or sub-unit dose. Whilst the dosage of hydroxypyrone iron complex given will depend on various factors, including the particular compound which is employed in the composition, it may be stated by way of guidance that maintenance at a satisfactory level of the amount of iron present in the human body will often be achieved using a daily dosage, in terms of the iron content of the compound, which lies in a range from about 0.1 to 100 mg and often in a range from 0.5 to 10 mg, for example 1 or 2 mg, veterinary doses being on a similar g/Kg body weight ratio. However, it will be appreciated that it may be appropriate under certain circumstances to give daily dosages either below or above these levels. In general, the aim should be to provide the amount of iron required by the patient without administering any undue excess and the properties of the pharmaceutical compositions according to the present invention are particularly suited to the achievement of this aim. Similarly, the concentration of iron in the pharmaceutical composition in the form of the hydroxypyrone complex may vary quite widely, for example over a range from about 0.001 to about 20% w/w. However, it is more usual for the concentration to exceed 0.01% w/w and it may often exceed 0.05 or 0.1% w/w, whilst a more usual limit for the upper end of the range is about 13% w/w. A common range of concentration is 0.05 to 5% w/w, for example 0.2 to 0.5, 1 or 2% w/w.

Where desired, more than one hydroxypyrone iron complex as described above may be present in the pharmaceutical composition or indeed other active compounds may be included in the composition, for example compounds having the ability to facilitate the treatment of anaemia, such as folic acid. Another additional component which may be included in the composition, if desired, is a source of zinc. Iron compounds used in the treatment of iron deficiency anaemia can inhibit the mechanism of zinc uptake in the body and this can cause serious side effects in the foetus when treating anaemia is in a pregnant female. It is believed, however, that the iron complexes of the present invention have a further advantage in that they either do not have this effect or exhibit the effect at a lower level than the compounds at present used in the treatment of anaemia. Accordingly, it may often be the case that the level of zinc providing compound added to the composition may not require to be high or, with preferred formulations of the iron complexes, may be dispensed with altogether.

A further approach to countering the effect of the acidic conditions prevailing in the stomach which is described in UK patent applications GB 2128998A involves formulation of the complex in the pharmaceutical composition together with the metal-free hydroxypyrone from which it is derived. The dissociation of the neutral 3:1 ferric complex involves various equilibria between this complex, the 2:1 and 1:1 complexes, and the metal-free compound, so that the presence of the latter will inhibit this dissociation. Any proportion of the free compound can be advantageous in this context but little further advantage accrues from increasing the proportion beyond a certain level, a suitable range for the molar proportion of the free compound which is present being from 0 to 100 moles of free hydroxypyrone:1 mole of iron complex, particularly of the neutral 3:1 iron(III) complex. Conveniently, a proportion of up to no more than 20, 30 or 50 moles:1 mole is used with a lower level of 0.5, 1 or 2 moles:1 mole. Although to obtain a marked effect upon dissociation of the iron complex by this means a proportion of at least 5 or 10 moles:1 mole is usually required, it should be emphasised that even a 1:1 molar ratio will achieve some degree of acid stabilisation of the iron complex.

It is possible to include amounts of the free hydroxypyrone in compositions according to the present invention, for example in a proportion as indicated above or particularly in a range of from 1 mole:10 or 20 moles of the iron complex. This is less likely in the context of the present invention to make a really marked contribution in terms of avoiding dissociation of the 3:1 complex since the nature of the compositions should insure that the major part of the iron complex is released in an essentially neutral environment. However, as described in the earlier application, the use of an uncomplexed hydroxypyrone in admixture with its iron complex may also have another advantage in addition to the prevention of dissociation of the iron complex under acidic conditions. Thus, in certain pathological conditions there may be an excess of iron deposited at certain sites even though the patient exhibits an overall anaemia. In these patients the use of such a mixture has the advantage that the iron complex will remedy the overall anaemia whilst the free hydroxypyrone will act to remove iron from pathological to physiological sites. However, although it is preferable for the hydroxypyrone present in an iron donor to be rapidly metabolized in order that iron may be efficiently transferred to the binding proteins and eventually to the iron requiring mechanisms without the body, it is preferable for a hydroxypyrone being used an iron remover not to be rapidly metabolized so that it remains in the system, taking up iron, for an extended period. Thus, for example, maltol is rapidly metabolized and is therefore particularly suited for use as an iron complex, but for this same reason it is not appropriate for use in the free form. It is also the case that different compounds may function more efficiently either in the free form as an iron remover or in complex form as an iron donor for quite other reasons. Alternatively, the different 3-hydroxy-4-pyrone may be replaced by a quite different form of iron chelating agent. Examples of such other iron chelating agents which may be used include the substituted 3-hydroxypyrid-2-ones and -4-ones, and 1-hydroxypyrid-2-one and substituted 1-hydroxypyrid-2-ones (and salts of these various pyridones with a physiologically acceptable cation) described in co-pending UK Patent Applications 8308056 (published as GB 2118176A), 8407181 (published as GB 2136807A) and 8423800 (claiming priority from UK Patent Application 8325496; to be published as GB 2146990A).

When a free hydroxy-4-pyrone, hydroxypyrid-2-one, hydroxypyrid-4-one, or other iron chelating agent is present in admixture with the iron complex of a hydroxy-4-pyrone for the purpose of acting as an iron remover, then the amount of this agent used may be different than when a free hydroxypyrone necessarily corresponding to that present in the iron complex is present primarily to prevent dissociation. Thus the daily dosage of the iron complex may be as above and the daily dosage of the free iron chelating agent, particularly when this is a hydroxypyrid-2- or -4-one or a 1-hydroxypyrid-2-one, may be that quoted in the co-pending applications referred to above, i.e. about 0.1 g to 5 g for human use, particularly 0.5 g to 2 g, from which it will be seen that the proportion of iron complex and free iron chelating agent used in such a context may extend across a wide range but preferred amounts of the free iron chelating agent tend to be higher than when this is necessarily a hydroxypyrone.

The present invention thus also includes a method for the treatment of a human or other mammalian patient to effect an increase in the level of iron in the patient's bloodstream which comprises administering to said patient an amount effective to achieve such an increase of a neutral 3:1-hydroxypyrone:iron(III) complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, said complex being administered through absorption by the membranes of the buccal cavity or the nasal passages. The administration is preferably effected by a composition which is retained in the mouth with consequent absorption by the membranes of the buccal cavity.

It will be appreciated from the foregoing discussion that it may happen that, in use, a proportion of the iron complex in a composition for buccal or nasal administration may be swallowed. However, particularly in view of the dissociation in the stomach of neutral 3:1 iron complex which is swallowed in a form unprotected from the acid conditions of the stomach, it will generally be the case that a major part of iron uptake will be by the membranes of the buccal cavity or the nasal passages and, indeed, iron uptake may often be essentially limited to this route.

Figure 1:
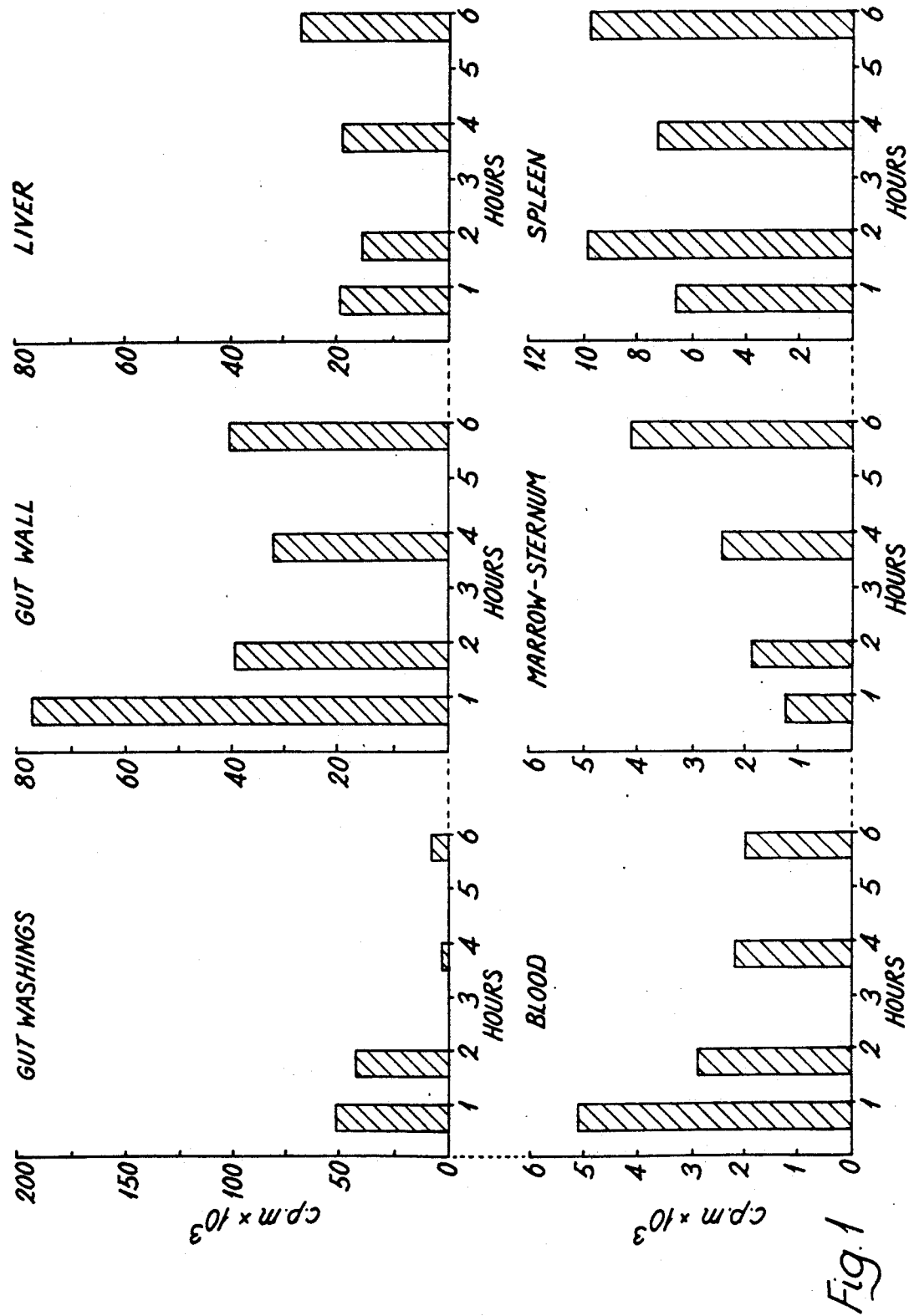
FIGS. 1-7 illustrates the results described in the following Examples.

This invention is illustrated by the following Examples:

EXAMPLES

Example 1

The Preparation of Iron Maltol

A chloroform solution of maltol is mixed with a 1M solution of ferric chloride in ethanol to provide a 3:1 molar ratio of malto:iron in the mixture. After 5 minutes at 20° C., a 10 molar excess of solid sodium carbonate is added and the mixture is stirred for 10 minutes. The mixture is then filtered and the solvent evaporated to give the neutral complex containing maltol and the ferric cation in 3:1 proportion. Recrystallisation of the 3:1 complex from ethanol gives wine red needle crystals in an essentially quantitative yield, m.p. 275°, $\gamma_{max}$ (nujol) 1600 cm$^{-1}$.

The use of an excess of maltol above the 3:1 molar ratio leads to an essentially quantitative yield of a solid mixture of the excess maltol and the 3:1 iron maltol complex on rotary evaporation, this mixture not being deliquescent.

The partition coefficient $K_{part}$ (concentration in n-octanol/concentration in aqueous phase) between n-octanol and Tris hydrochloride (20 mM, pH 7.4) of maltol and of its 3:1 iron complex is measured at $10^{-4}$M by spectrophotometry. Acid washed glassware is used throughout and, following mixing for 1 minute, the aqueous/n-octanol mixture is centrifuged at 1000 g for 30 seconds. The two resulting phases are separated for a concentration determination by spectrophotometry on each. For maltol, the range 220-340 nm is used for the concentration determination whilst for the complex the range 340-640 nm is used. Typically, a value of 0.66 is obtained for maltol and of 0.50 for its iron complex, whilst comparative experiments on iron(III) EDTA and iron(III) ascorbate give much smaller values of 0.001 and 0.0015, respectively.

The ability of the iron complex of maltol to bind to hemoglobin is investigated by studying the elution profile of a $^{59}$Fe label when a mixture of haemoglobin and the $^{59}$Fe-labelled complex (at 1 mM concentration) in NaCl (130 mM) buffered to pH 7.4 by Tris hydrochloride is applied to a PD-10 column (Sephadex G-10 gel permeation column - Pharmacia). Typically, no evidence is found for binding of the complex to haemoglobin which is an advantageous finding since such binding reduces availability of the iron.

The ability of the iron complex of maltol to bind to bovine serum albumen (BSA) is investigated through a similar procedure in which the complex is applied to a column with BSA rather than haemoglobin. The iron complex also shows little ability to bind to BSA.

EXAMPLE 2

In Vitro Tests on Permeation of Iron Complexes into Human Erythrocytes

The accumulation of iron by human erythrocytes which are associated with the iron complex of maltol described in Example 1, and various other iron compounds by way of comparison, was studied by incubating the erythrocytes for 1 hour at 37° C. in a medium consisting of the $^{59}$Fe labelled iron compound in aqueous sodium chloride (130 mM) buffered to a pH of 7.4 by Tris hydrochloride. Following this period of incubation an aliquot of the erythrocyte/medium mixture was placed above a layer of silicone oil ($\rho = 1.06$) and the erythrocytes separated by centrifugation through the oil. The $^{59}$Fe levels associated with the erythrocytes and the incubation medium were then counted and presented as a distribution ratio (concentration in erythrocytes/concentration in medium). The ratios obtained for the various iron compounds after incubation for 1 hour are shown in Table 1 where it will be seen that the uptake of iron is clearly much greater with the iron maltol complex than with the other compounds. Values of less than 0.1 are probably associated with binding to the external surface and do not represent transmembrane movement of iron. Moreover, although a period of 1 hour was employed in order to facilitate monitoring of the more slowly permeating iron compounds, the uptake of the iron maltol complex reached equilibrium at the level shown after about 15 minutes.

TABLE 1

| Compound | Concentration (mM) | Distribution ratio |
| --- | --- | --- |
| $Fe^{III}$ (maltol)$_3$ | 3 | 1.60 |
| $Fe^{II}$ gluconate | 1 | 0.08 |
| $Fe^{III}$ ascorbate | 1 | 0.12 |
| $Fe^{III}$ citrate | 1 | 0.05 |
| $Fe^{III}$ EDTA | 1 | 0.05 |

When the above described procedure was applied using ratios of maltol to iron of less than 3:1 larger apparent distribution ratios were observed than 1.60. However, this is explained by the non-specific binding of the positively charged 2:1 and 1:1 maltol:iron complexes to the surface of the erythrocytes which possesses a net negative charge, being rich in both phosphate and sulphate moieties. Experiments to determine the percentage of $^{59}$Fe associated with erthrocyte ghosts after lysis confirm this hypothesis. In one experiment, lysis was initiated by a small volume of 10% v/v Triton X100 and in a second experiment by a 10 fold excess of water. In each case the resulting ghosts were centrifuged through silicone oil ($\rho = 1.02$) and, as will be seen from Table 2, very little of the 3:1 maltol:iron complex was found to be bound to the membranes, in contrast with the situation with the 2:1 and 1:1 complexes. Such binding is of course undesirable as the complex is likely to remain tightly bound to the membrane by electrostatic interactions and not be transmitted across it.

TABLE 2

| Ratio of maltol:iron | Iron associatied with with ghosts (%) | |
| --- | --- | --- |
| | Triton lysis | Hypotonic lysis |
| 0:1 | 100 | — |
| 1:1 | 55 | 63 |
| 2:1 | 22 | 39 |
| 3:1 | <1 | <5 |

EXAMPLE 3

In Vitro Tests on Permeation of Rat Jejunal Sac by Iron Complexes

The iron uptake into the serosal space of the rat jejunal sac was compared for the iron complex of maltol described in Example 1 and various other iron compounds by way of comparison. Rats (male Sprague Dawley, 60 g) were killed and the jejunum removed, everted and cut into three segments (4 cm length). The segments were tied at both ends, filled with Krebs Ringer buffer (0.2 ml) and incubated in Krebs Ringer buffer containing the appropriate $^{59}$Fe compound at 37° C. for periods up to 90 minutes. The contents of the sac were counted for $^{59}$Fe and measured spectrophotometrically.

The results obtained for the iron maltol complex and for 6 other iron compounds which are each contained in preparations marketed for the treatment of iron deficiency anaemia are shown in Table 3, the iron uptake for each at 15 and 60 minutes after the initiation of the experiment being shown relative to that for ferric chloride as 1. It will be seen that the iron maltol complex provides a level of iron uptake which is significantly higher than the levels observed for any of the 6 compounds in current use for the treatment of iron deficiency anaemia. The uptake of the iron maltol complex was linear for a period of 90 minutes. Moreover, the uptake increased linearly as the concentration of the complex was increased over a range from 0.5 to 10 mM, so it does not show saturation kinetics and the process is thus non-facilitated and therefore should occur in all natural membranes.

TABLE 3

| Compound | Relative iron uptake | |
| --- | --- | --- |
| | 15 minutes | 60 minutes |
| FeCl$_3$ | 1 | 1 |
| $Fe^{III}$ (maltol)$_3$ | 40 | 5.8 |
| $Fe^{II}$ sulphate | 2.4 | 1.4 |
| $Fe^{II}$ fumarate | 4.0 | 1.8 |
| $Fe^{II}$ gluconate | 1.6 | 0.8 |
| $Fe^{II}$ succinate | 2.0 | 1.0 |
| $Fe^{III}$ ascorbate | 0.4 | 0.8 |
| $Fe^{III}$ citrate | 2.0 | 1.8 |

The procedure described above was used to compare the uptake of iron from buffer containing differing molar proportions of maltol:iron. The results obtained are presented in Table 4 which shows the amount of iron transferred via the maltol complex into the serosal contents of the sac, the basal uptake of iron measured in a control experiment being subtracted in each case. It will be seen that the amount of iron transferred in the case of a 3:1 molar proportion of maltol:iron(III) is much higher than in the other two cases and, moreover, the low, but significant level of iron uptake observed in the case of a 2:1 ratio is attributed to the proportion of the 3:1 complex (containing 13% of the total iron) present under these conditions.

TABLE 4

| Maltol/iron (molar ratio) | Iron uptake (n mole) |
| --- | --- |
| 1:1 | 1.6 |
| 2:1 | 4.0 |
| 3:1 | 30.0 |

EXAMPLE 4

In Vivo Test of Action of Iron Compounds in the Rat

The action of the iron complex of maltol described in Example 1 was compared with that of iron(II) sulphate, iron(III) EDTA (1:1 molar ratio) and iron(II) gluconate.

Groups of rats (300–350 g) were anaesthetised with nembutal (0.25 ml) and then with ether. A mid-line incision was made and the $^{59}$Fe labelled sample (100 μg Fe, 10 μCi) was passed into the lumen of the duodenum via a small incision. The abdominal well was then closed with a suture. The animals were sacrificed 1, 2, 4 and 6 hours after the administration of the compound and the various organs were monitored for their $^{59}$Fe content. The data is presented as histograms in FIGS. 1 to 4 which relate to iron maltol, iron sulphate, iron EDTA and iron gluconate, respectively, and show the levels of $^{59}$Fe in cpm after various time intervals for the different organs, the data in each case representing a mean of the results for three individual animals. In the case of the data for blood and sternum (bone marrow) the counts given are cpm/ml and cpm/g respectively, whilst in all other cases they are the total cpm counts. The various histograms have been normalised and consequently are directly comparable.

Figure 2:
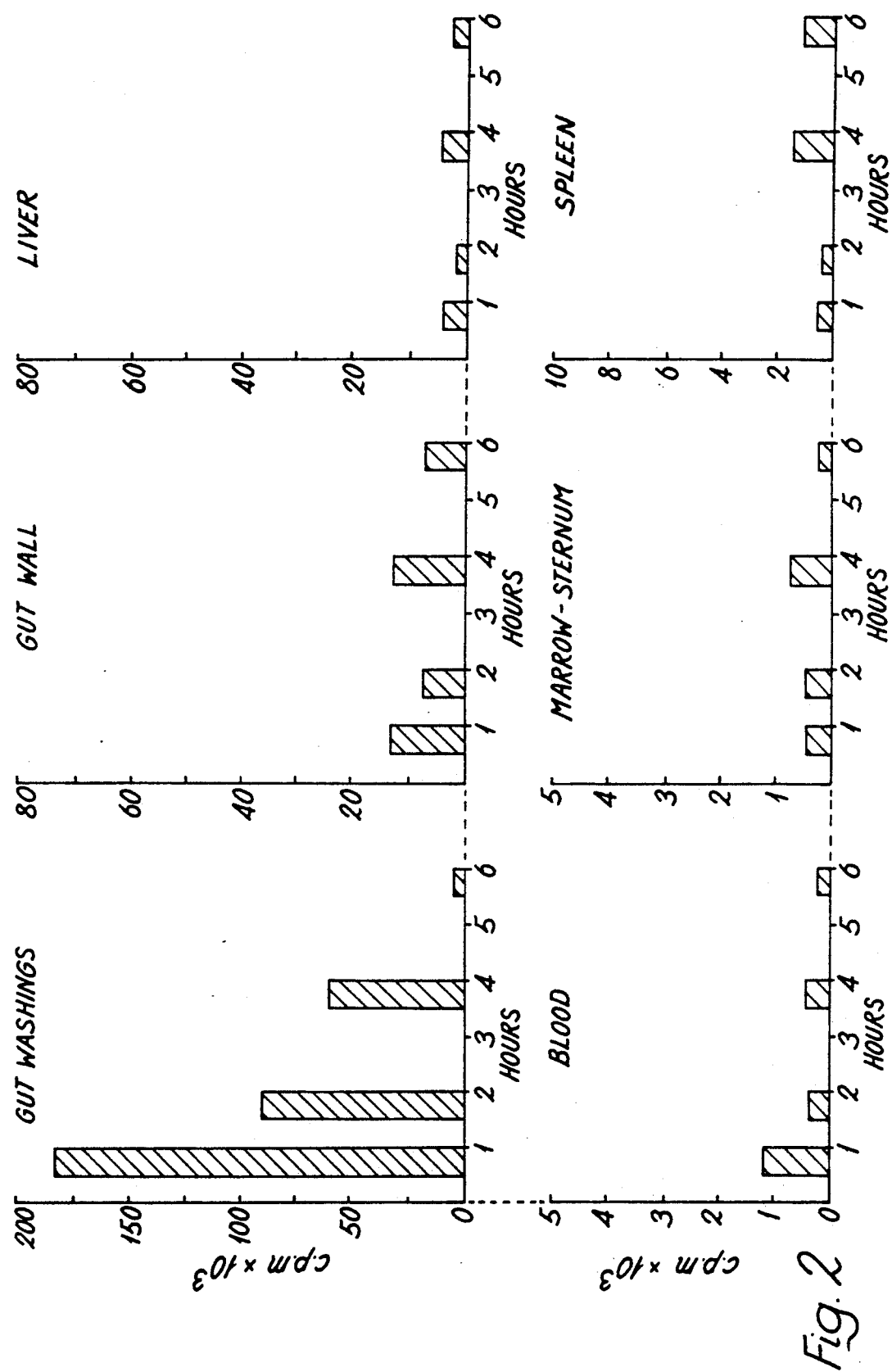

A comparison between FIGS. 1 and 2 shows that the neutral 3:1 maltol:iron(III) complex is markedly superior to iron(II) sulphate for the introduction of iron via the rat intestine. The gut washings (which contain non-absorbed iron) show a much lower level of counts for the maltol complex, and the counts associated with the gut wall, liver, blood, bone marrow and spleen are correspondingly greater. It is clear from FIG. 1 that $^{59}$Fe associated with maltol enters the intestine wall very rapidly and from there it is efficiently removed by the blood supply. Iron is deposited in the bone marrow continuously throughout the 6 hour period at an apparently constant rate.

Figure 3:
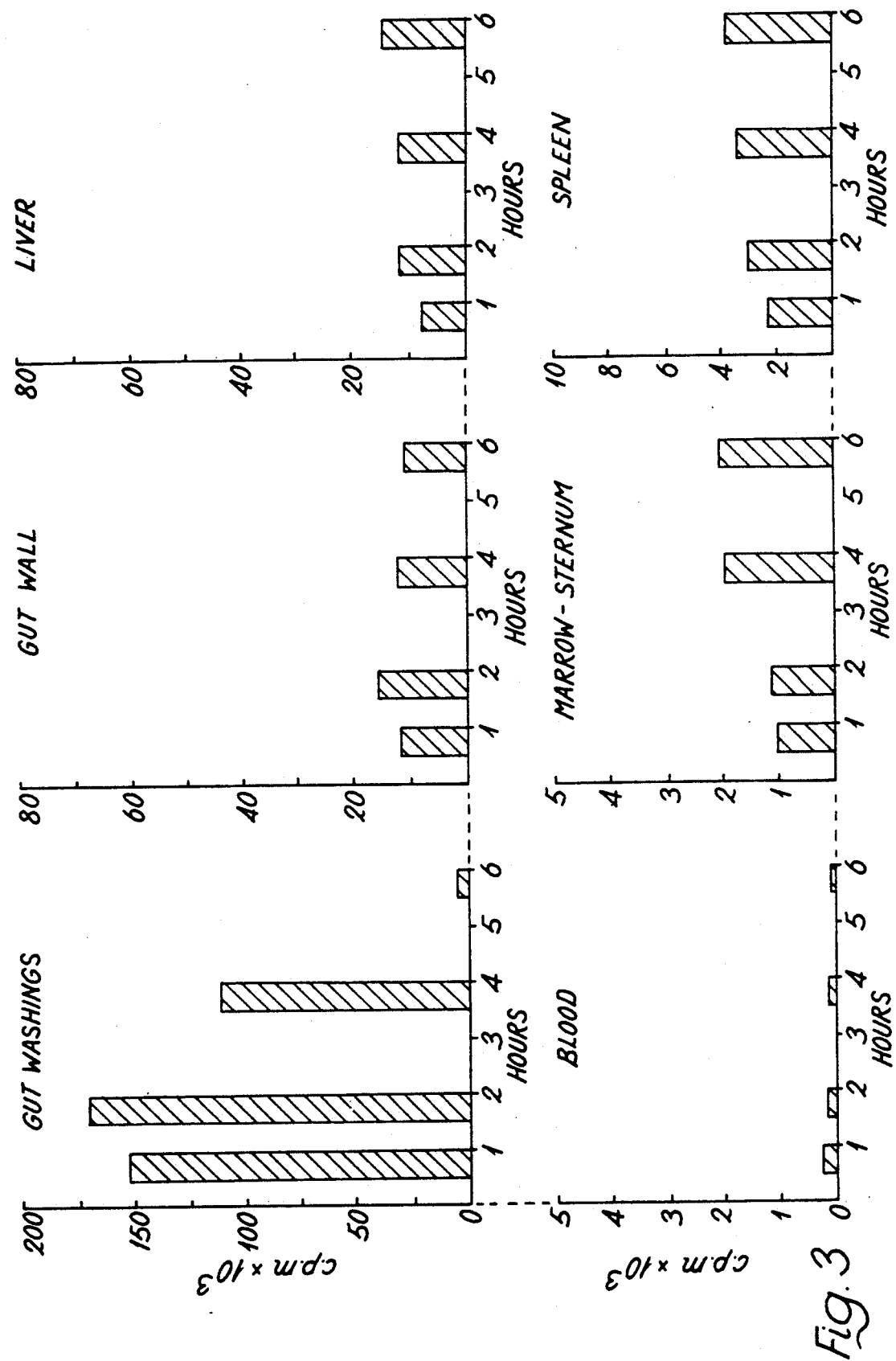
Figure 4:
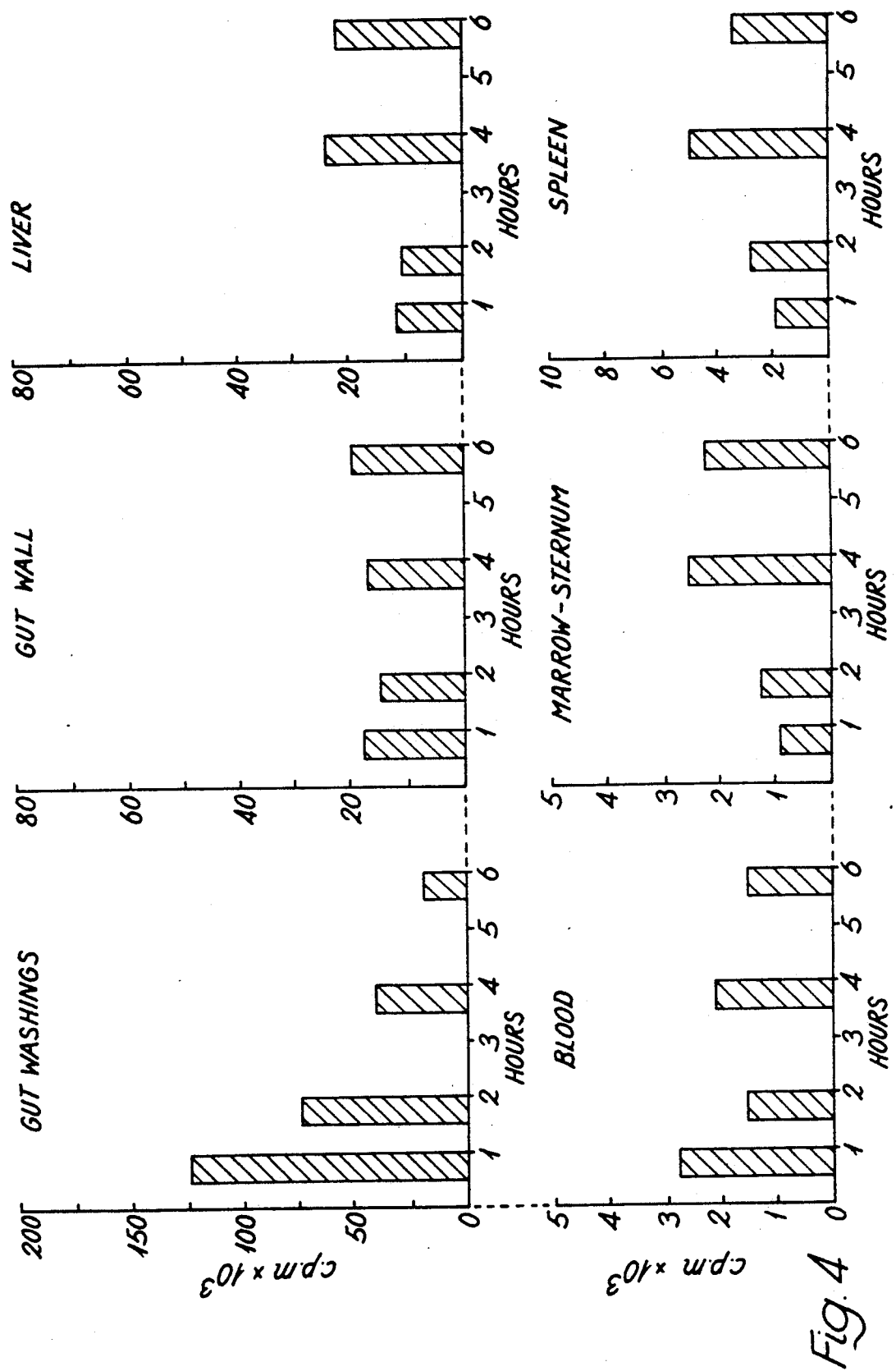

The maltol complex is also more efficient than iron(III) EDTA as shown by FIG. 3. With the later complex, the gut washings remain high for 4 hours and may be presumed to decrease only due to the effect of natural bowel movements translocating material from the portion under investigation to lower portions of the intestine. The levels in the intestine wall and blood are extremely low. Although iron is transferred to both bone marrow and spleen, this is at reduced rates as compared to those obtained with the maltol complex. As shown by FIG. 4, iron(II) gluconate proved more effective than the sulphate or the EDTA complex, although deposition in the gut wall was less than that observed with the maltol complex. The decrease was reflected in the lower levels of $^{59}$Fe in both bone marrow and the spleen, the difference being particularly marked after 6 hours. In view of the much higher levels of $^{59}$Fe trapped in the intestine wall in the case of the maltol complex, it may be predicted that this compound facilitates a more prolonged supply of iron than iron(II) gluconate.

This test illustrates the superiority of the neutral 3:1 maltol:iron(III) complex as compared with three commonly used "soluble iron" preparations for the movement of iron across the rat jejunal wall into the blood circulation, the iron maltol being very rapidly removed from the lumen of the intestine.

EXAMPLE 5

In Vivo Test of Action of Iron Complexes in the Cat

The action of the iron complex of maltol described in Example 1 was compared with that of iron(III) EDTA (1:1 molar ratio) which is one of the iron compounds currently marketed for the treatment of iron deficiency anaemia. Cats were anaesthetised with chloralase (60 mg/kg) and pentobarbitone sodium (60 mg/kg) (i.p.), having been kept free of food for 18 hours. In each animal the trachea was cannulated to maintain a clear airway and to allow positive pressure artificial respiration if necessary. The left femoral vien was cannulated for the intravenous administration of drugs and physiological saline solution. Arterial blood pressure was monitored by a Washington pressure transducer through a cannula inserted into the femoral artery of the right hind leg. Arterial blood samples were taken at appropriate intervals from a short cannula inserted into an external carotid artery. Body temperature was monitored with a rectal thermometer. Each animal was given heparin (1000 iu/kg) as anticoagulant and additional small amounts of pentabarbitone sodium if needed to maintain a satisfactory level of anaesthesia.

In those animals where the iron compounds were to be administered into the duodenum, a mid-line incision was made in the abdomen to reveal the intestines. A cannula was then inserted through a small cut such that its tip rested approximately 5 cm below the opening of the bile duct. The cannula was then sutured in place and the abdominal wall closed with stitches.

The iron maltol complex (100 μg Fe) alone (3:1 molar ratio of maltol:iron) and together with a large excess of maltol (40:1 molar ratio of maltol:iron) was injected intravenously in separate experiments and 0.25 ml samples of blood were taken at intervals. The apparent volume of distribution of the compound was calculated by extrapolation of the log-linear blood concentration curve to zero. (The volume corresponds to a value between that of the total extracellular space of the animal and the blood volume.) Elimination of $^{59}$Fe from the blood followed first order kinetics with a rate constant of $-0.022$/minute in the presence and absence of excess maltol, as illustrated in FIG. 5 which shows the $^{59}$Fe level in the blood in cpm/0.25 ml plotted against time in the case of one typical experiment of each type in an individual cat.

Figure 5:
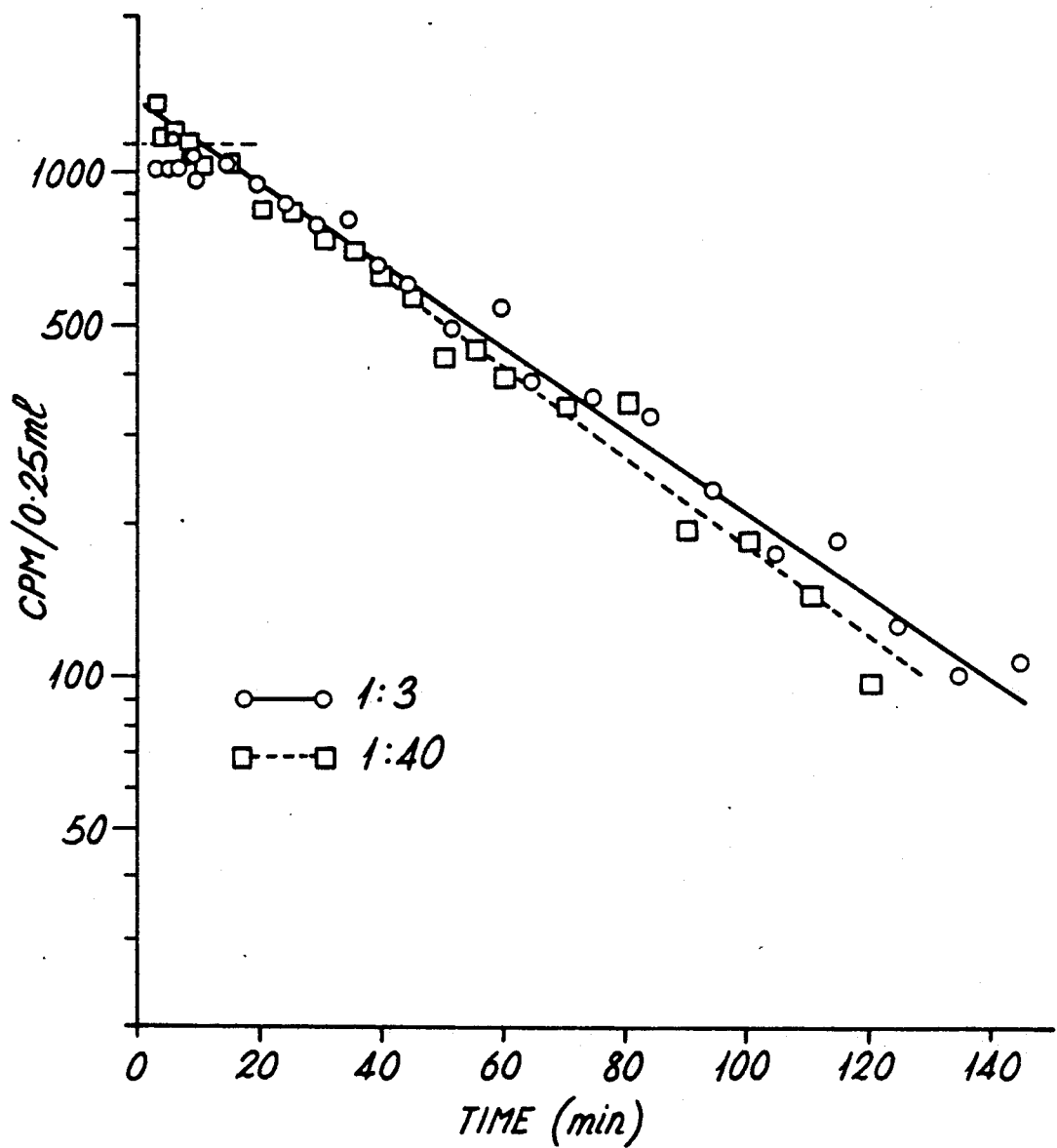

The distribution of $^{59}$Fe in the tissues of the animal after the same intravenous experiment to which FIG. 5 relates (the lower end of the ordinate in this Figure represents the background level) was investigated and the typical results are shown in Table 5. The amount of $^{59}$Fe administered in this experiment was 4 μCi of $2.2 \times 10^6$ cpm. It will be seen that approximately 10% of the dose was located in the combined tissue of the heart, liver and spleen. As less than 0.2% of the dose was located in the urine, the bulk (approximately 90%) of the $^{59}$Fe was almost certainly directed to the bone marrow and extremely high levels were found to be located in the sternum.

As indicated previously, the maltol complex is able to donate iron rapidly to transferrin and it is hypothesised that such an exchange occurs as soon as the complex is delivered to the plasma; and that the initial plateau (represented in FIG. 5 by a dotted line) represents saturation of the plasma transferrin pool with $^{59}$Fe. When there is net donation of $^{59}$iron from the plasma into the organs of the animal, the blood levels of radioactivity begin to fall, the major route of transfer of iron bound to transferrin being to the bone marrow, liver and spleen. Binding of $^{59}$Fe to transferrin prevents its excretion in the urine.

TABLE 5

(Iron maltol, i.v)

| Tissue | Total tissue weight (g) | Sample weight (g) | Net $^{59}$Fe content (cpm/g) | Net total $^{59}$Fe content (cpm) |
|---|---|---|---|---|
| Heart | 14.4 | 0.91 | 490 | 7,056 |
| Liver | 105 | 1.3 | 510 | 53,550 |
| Spleen | 8.4 | 0.86 | 14,890 | 125,076 |
| Kidney | 12.2 | 1.05 | 546 | 6,661 |
| Skeletal muscle | — | 1.85 | 0 | 0 |
| Sternum (bone marrow) | — | 1.2 | 3,200 | — |
| Urine | — | 1 | 152 | <3,000 |

Figure 6:
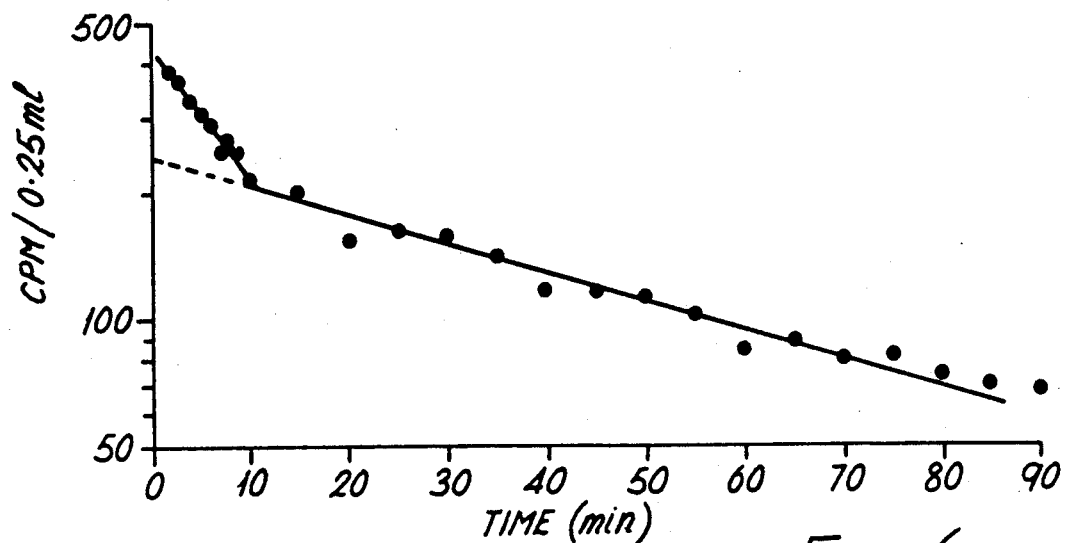

Identical experiments carried out with $^{59}$Fe labelled iron(III) EDTA gave a entirely different picture as will be seen for the results of a typical experiment illustrated in FIG. 6 (in which the lower end of the ordinate represents the background level) and Table 6 (the amount of $^{59}$Fe administered in this experiment was 2 $\mu$Ci but the figures given in the table have been adjusted to correspond to a dosage of 2.2 × 10$^6$ cpm in order to facilitate comparison with Table 5). In this experiment the radioactivity in the blood showed no initial plateau. Instead, loss of radioactivity followed at least a two-component process such that a large amount found its way to the urine rather than to the tissues. The rate constant of the elimination from the blood of the linear phase of the regression was 0.023/minute. The concentration of radioactivity in the kidney and urine, and not in the bone marrow or spleen, would indicate that iron in this form does not appear to be able to attach to transferrin in the plasma and protect itself from urinary excretion. The combined tissue of heart, liver and spleen contained only 1% of the original dose at the end of the experiment, whereas the urine contained over 50%. This is in accord with the fact that EDTA does not exchange iron with transferrin rapidly.

TABLE 6

(Iron EDTA, i.v.)

| Tissue | Total tissue weight (g) | Sample weight (g) | Net $^{59}$Fe content (cpm/g) | Net total $^{59}$Fe content (cpm) |
|---|---|---|---|---|
| Heart | 15.5 | 1.01 | 209 | 3,248 |
| Liver | 75 | 1.21 | 261 | 19,600 |
| Sternum (bone marrow) | — | 0.28 | 1,164 | — |
| Spleen | 11.2 | 0.89 | 162 | 1,814 |
| Kidney | 19.2 | 1.47 | 1,134 | 21,770 |
| Skeletal muscle | — | 2.59 | 95 | — |
| Urine | 19 ml | 2 ml | 62,156 | 1,180,900 |

Figure 7:
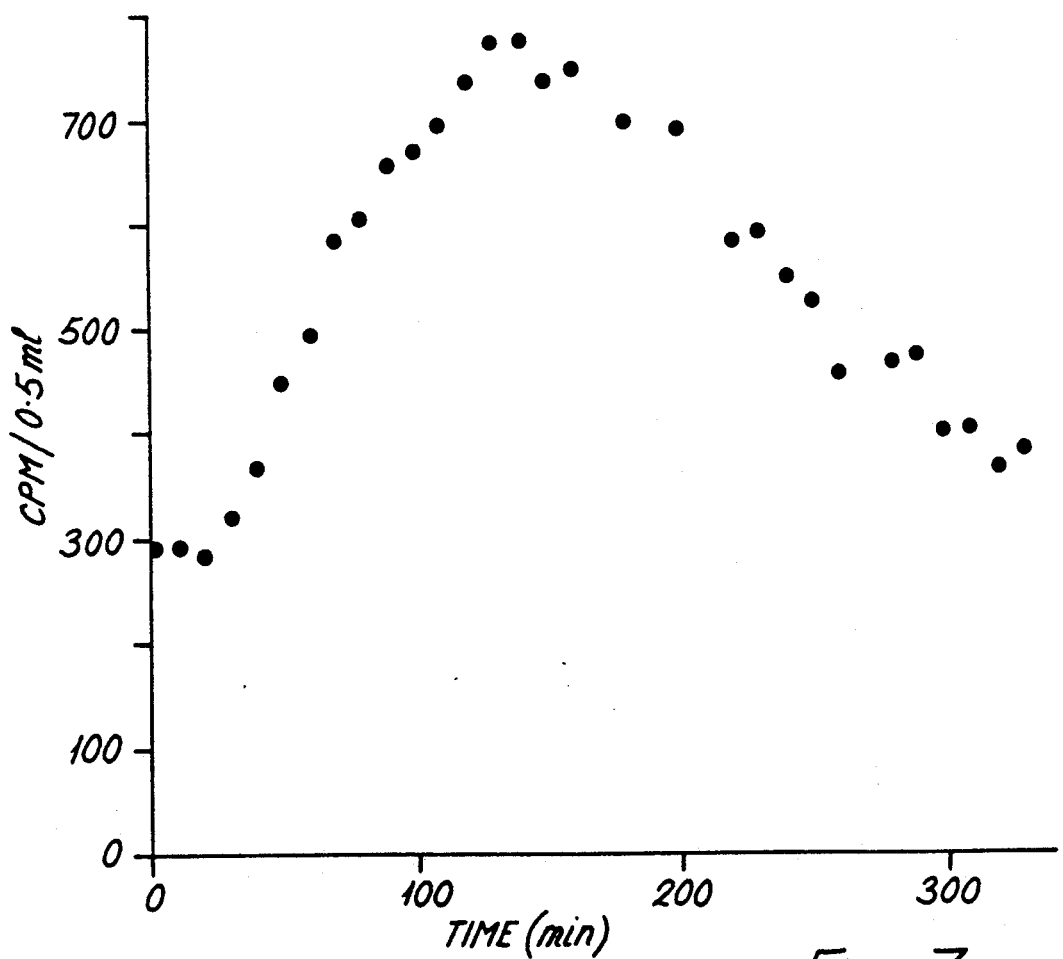

The iron maltol complex (100 $\mu$g Fe) was also administered to the duodenum of the cat in the presence of a 40 fold excess of maltol followed by 5 ml of 150 ml Tris hydrochloride buffer (pH 7.4). In this case the $^{59}$Fe content of the blood, as shown in FIG. 7, reaches a maximum level 2 hours after the initial administration (the readings start at about 300 cpm/0.5 ml which represents the background reading). The distribution of $^{59}$Fe in the tissues of the animal after the same duodenal experiment to which FIG. 7 relates were investigated and the typical results are shown in Table 7. The amount of $^{59}$Fe administered in this experiment was 10 $\mu$Ci or 5.327 × 10$^6$ cpm into a 2.9 kg cat. It will be seen that the distribution of the $^{59}$Fe after 4 hours was similar to that after intravenous infusion, with low levels in the kidney and urine and high levels in both the spleen and bone marrow.

TABLE 7

(Iron maltol, per duodenum)

| Tissue | Total tissue weight (g) | Sample weight (g) | Net $^{59}$Fe content (cpm/g) | Net total $^{59}$Fe content (cpm) |
|---|---|---|---|---|
| Heart | 14 | 0.633 | 50 | 1,106 |
| Liver | 81 | 1.45 | 400 | 32,400 |
| Spleen | 12.7 | 1.19 | 3,783 | 48,047 |
| Kidney | 14.4 | 0.835 | 79 | 1,138 |
| Sternum (bone marrow) | 10 | 1.26 | 790 | 7,905 |
| Bile | ~5 ml | 1 ml | 2,200 | ~11,000 |
| Urine | ~10 ml | 1 ml | 22 | ~220 |

When $^{59}$Fe labelled iron(III) EDTA was administered duodenally in the same manner, the plasma levels of radioactivity hardly exceeded the background level and are therefore not illustrated in a Figure. The distribution of $^{59}$Fe in the tissues of the animal after the same duodenal experiment were investigated and the typical results are shown in Table 8. The amount of $^{59}$Fe administered in this experiment was 10 $\mu$Ci or 2.65 × 10$^6$ cpm into a 2.9 kg cat. It will be seen that, although some $^{59}$Fe entered the tissues, rather low levels were detected in the spleen and bone marrow (sternum) whereas a large proportion of the dose was located in the urine.

TABLE 8

(Iron EDTA, per duodenum)

| Tissue | Total tissue weight (g) | Sample weight (g) | Net $^{59}$Fe content (cpm/g) | Net total $^{59}$Fe content (cpm) |
|---|---|---|---|---|
| Heart | 15.3 | 1.18 | 188 | 2,878 |
| Liver | 59.3 | 0.78 | 499 | 29,574 |
| Kidney | 11.3 | 0.90 | 1,762 | 19,913 |
| Spleen | 4.4 | 0.42 | 200 | 880 |
| Sterum (bone marrow) | — | 0.78 | 917 | — |
| Skeletal muscle | — | 1.48 | 117 | — |
| Urine | 15 ml | 5 ml | 36,306 | 544,596 |

EXAMPLE 6

Formulation

In a formulation utilising a pastille base described in the 1973 edition of Martindale, the Extra Pharmacoepia, but with the replacement of bordeaux B by amaranth, pastilles are prepared from the following ingredients: 3:1 maltol:iron(III) complex, 0.25 g; gelatin, 20 g; glycerin, 40 g; sucrose, 5 g; citric acid, 2 g; sodium benzoate, 0.2 g; oil of lemon, 0.1 ml; concentrated orange flavour water, 0.52 ml; solution of amaranth, 1.04 ml; and water to a total weight of 100 g.

The gelatin is mixed with one and a half times its volume of water and the glycerin is added to the mixture, the product being heated on a water bath until a solution is produced. The iron maltol, sucrose, citric acid, sodium benzoate and amaranth are then added as a solution in a small volume of water. The solution is cooled, orange flavour water and oil of lemon are added, and the remaining water is added to bring the weight of the mixture to 100 g. The mixture is then strained through muslin, poured into a pastille mould and allowed to dry to give pastilles containing approximately 5 mg of iron maltol.

We claim:

1. A pharmaceutical composition for alleviating iron-deficiency anemia comprising an effective amount of a neutral 3:1 hydroxypyrone:iron(III) complex of 3-hydroxy-4-pyrone or of a 3-hydroxy-4-pyrone in which one or more of the hydrogen atoms attached to the ring carbon atoms are replaced by an aliphatic hydrocarbon group of 1 to 6 carbon atoms, said composition being in aerosol form.

2. The pharmaceutical composition according to claim 1, in which the complex is of a 3-hydroxy-4-pyrone in which one or more of the hydrogen atoms attached to ring carbon atoms are replaced by the same or different substituents selected from the group consisting of methyl, ethyl, n-propyl and isopropyl groups.

3. The pharmaceutical composition according to claim 2, in which one or more of the hydrogen atoms attached to ring carbon atoms are replaced in the substituted 3-hydroxy-4-pyrone.

4. The pharmaceutical composition according to claim 3, in which the substituted 3-hydroxypyrone has a single substituent.

5. The pharmaceutical composition according to claim 4, in which the single substituent is at the 2- or 6-position.

6. The pharmaceutical composition according to claim 1, in which the complex is the 3:1 iron complex of 3-hydroxy-4-pyrone, 3-hydroxy-2-methyl-4-pyrone, 3-hydroxy-6-methyl-4-pyrone or 2-ethyl-3-hydroxy-4-pyrone.

7. The pharmaceutical composition according to claim 1 which additionally contains an iron chelating agent.

8. The pharmaceutical composition according to claim 7, in which the iron chelating agent is uncomplexed 3-hydroxy-4-pyrone or an uncomplexed 3-hydroxy-4-pyrone in which one or more of the hydrogen atoms attached to ring carbon atoms are replaced by an aliphatic hydrocarbon group of 1 to 6 carbon atoms, or a salt thereof containing a physiologically acceptable cation.

9. The pharmaceutical composition according to claim 8, which contains a complexed hydroxypyrone together with the same hydroxypyrone or a salt thereof in uncomplexed form.

10. The pharmaceutical composition according to claim 8, which contains a complexed hydroxypyrone together with a different hydroxypyrone or a salt thereof in uncomplexed form.

11. The pharmaceutical composition according to claim 1, which additionally contains folic acid.

12. A method for increasing the level of iron in a patient's bloodstream which comprises administering to said patient by the buccal or nasal route an amount effective to achieve said increase of a compound being a neutral 3:1 hydroxypyrone:iron(III) complex of 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms.

13. The method according to claim 12, in which each aliphatic hydrocarbon group is an acyclic alkyl group of 1 to 4 carbon atoms.

14. The method according to claim 12, in which the compound is an iron complex of a 3-hydroxy-4-pyrone in which one or more of the hydrogen atoms attached to ring carbon atoms are replaced by the same or different substituents selected from the group consisting of methyl, ethyl, n-propyl and isopropyl.

15. The method according to claim 14, in which one or two of the hydrogen atoms attached to ring carbon atoms are replaced in the substituted 3-hydroxy-4-pyrone.

16. The method according to claim 15, in which the substituted 3-hydroxypyrone has a single substituent.

17. The method according to claim 16, in which the single substituent is at the 2- or 6-position.

18. The method according to claim 20, in which the compound is the 3:1 iron complex of 3-hydroxy-4-pyrone, 3-hydroxy-2-methyl-4-pyrone, 3-hydroxy-6-methyl-4-pyrone or 2-ethyl-3-hydroxy-4-pyrone.

19. The method according to claim 18, in which the compound is the 3:1 iron complex of 3-hydroxy-2-methyl-4-pyrone.

20. The method according to claim 18, in which the compound is the 3:1 iron complex of 2-ethyl-3-hydroxy-4-pyrone.

21. The method according to claim 12, in which the compound is administered by the buccal route.

22. The method according to claim 21, in which administration is by chewing or sucking a solid composition containing the compound.

23. A pharmaceutical composition for alleviating iron-deficiency anemia which is in a form adapted for retention in the mouth without swallowing the same, to thereby release the active component of the composition, which comprises an effective amount of a neutral 3:1 hydroxypyrone:iron (III) complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms; and a pharmaceutically acceptable carrier.

24. The pharmaceutical composition according to claim 23, in which the complex is of a 3-hydroxy-4-pyrone in which one or more of the hydrogen atoms attached to ring carbon atoms are replaced by the same or different substituents selected from the group consisting of methyl, ethyl, n-propyl and isopropyl groups.

25. The pharmaceutical composition according to claim 24, in which one or two of the hydrogen atoms attached to ring carbon atoms are replaced in the substituted 3-hydroxy-4-pyrone.

26. The pharmaceutical composition according to claim 25, in which the substituted 3-hydroxypyrone has a single substituent.

27. The pharmaceutical composition according to claim 26, in which the single substituent is at the 2- or 6-position.

28. The pharmaceutical composition according to claim 23, in which the complex is the 3:1 iron complex of 3-hydroxy-4-pyrone, 3-hydroxy-2-methyl-4-pyrone, 3-hydroxy-6-methyl-4-pyrone or 2-ethyl-3-hydroxy-4-pyrone.

29. The pharmaceutical composition according to claim 23, which further contains an iron chelating agent.

30. The pharmaceutical composition according to claim 29, in which the iron chelating agent is uncomplexed 3-hydroxy-4-pyrone or an uncomplexed 3-hydroxy-4-pyrone in which one or more of the hydrogen atoms attached to ring carbon atoms are replaced by an aliphatic hydrocarbon group of 1 to 6 carbon atoms, or a salt thereof containing a physiologically acceptable cation.

31. The pharmaceutical composition according to claim 30, which contains a complexed hydroxypyrone together with the same hydroxypyrone or a salt thereof in uncomplexed form.

32. The pharmaceutical composition according to claim 30, which contains a complexed hydroxypyrone together with a different hydroxypyrone or a salt thereof in uncomplexed form.

33. The pharmaceutical composition according to claim 23, which additionally contains folic acid.

34. The pharmaceutical composition according to claim 23, which contains a solid carrier and is adapted for chewing or sucking.

35. The pharmaceutical composition according to claim 34, wherein said composition is in the form of pastilles or lozenges.

36. The pharmaceutical composition according to claim 23, which is in unit dosage form.

* * * * *

UNITED STATES PATENT AND TRADEMARK OFFICE
CERTIFICATE OF CORRECTION

PATENT NO. : 5,028,411

DATED : July 2, 1991

INVENTOR(S) : CALLINGHAM et al

It is certified that error appears in the above-identified patent and that said Letters Patent is hereby corrected as shown below:

Title page of the patent under [75] delete "Brian A. Callingham, Cambridge;"

Title page of the patent, left hand column under "U.S. PATENT DOCUMENTS" last line delete "Hilder et al" and replace by --Hider et al--

Title page of the patent, right hand column continue the list of "OTHER PUBLICATIONS" with the following references:

Johnson & Thomas, Pharmaceutical Society of Great Britain Scientific Publications Department, pp. 1037-1047, "The Stability of Aqueous Solutions of Ferrous Gluconate"

Gerard & Hugel, J. Chem. Research (S), 1980, p.314, "Iron(III) Complexes of Maltol (3-Hydroxy-2-methyl-4-pyrone), including Hydroxo-complexes in an Acidic Medium"

Habeeb et al, J. Coord. Chem. (1978), $\underline{8}$, 27-33, "Direct Electrochemical Synthesis of some Metal Chelate Complexes"

Grady et al "J. of Pharm. & Exp. Therapeutics (1976), $\underline{196}$, 478-485, "The Development of New Iron-Chelating Drugs"

Ganeshaguru et al, Biochem. Pharmacol. (1980), $\underline{29}$, 1275-1279, "Effect of Various Iron Chelating Agents on DNA Synthesis in Human Cells"

UNITED STATES PATENT AND TRADEMARK OFFICE
CERTIFICATE OF CORRECTION

PATENT NO. : 5,028,411

DATED : July 2, 1991

INVENTOR(S) : CALLINGHAM et al

It is certified that error appears in the above-identified patent and that said Letters Patent is hereby corrected as shown below:

White et al, Brit. J. Haem. (1976), 33, 487-495, "The Use of Chang Cells Culture in vitro to Evaluate Potential Iron Chelating Drugs"

Stefanovic et al, Collection Czech. Chem. Commun. (1968), 33, 4198-4214, "On the Reaction of Iron (III) with Maltol"

Lieberman & Lachman, Pharmaceutical Dosage Forms (1982), 3, 165-167, Marcel Decker E. Jones, Manufacturing Chemist & Aerosol News, May 1970, "Production of Enteric Coated Capsules"

Blake, undated, "Study to Compare the Effect of Iron Maltol versus Ferrous Sulphate in the Correction of Chronic Iron Deficiency Anaemia"

Maxton et al, January 1986, "Report of Iron Uptake from Fe (III) Maltol", Human Studies Skikne, February 14, 1986. Letter Hider, Structure and Bonding (1984), 58, 25-87 "Siderophore Mediated Absorption of Iron"

UNITED STATES PATENT AND TRADEMARK OFFICE
CERTIFICATE OF CORRECTION

PATENT NO. : 5,028,411

DATED : July 2, 1991

INVENTOR(S) : CALLINGHAM et al

It is certified that error appears in the above-identified patent and that said Letters Patent is hereby corrected as shown below:

The Merck Index (1976), 9th Edition, Merck & Co., Inc. Rahway, N.J., 543-544

Abandoned USSN 310,141 to Tate et al

Kidani et al, Nagoya Shiritsu Daigaku Yakugakubu Kenkyu Nempo (1970), 18, 16-21, "Synthesis of Maltol-Fe (III) Complex"

Chemical Abstracts, 75:115362k (1971)

Chemical Abstracts, 94:41144j (1981)

Chemical Abstracts, 94:24201h (1981)

Chemical Abstracts, 94:156749c (1981)

Chemical Abstracts, 98:71930n (1983)

Foye & Lo, J. Pharm. Sci. (1972), 61, 1209-1212, "Metal-Binding Abilities of Antibacterial Heterocyclic Thiones"

UNITED STATES PATENT AND TRADEMARK OFFICE
CERTIFICATE OF CORRECTION

PATENT NO. : 5,028,411

DATED : July 2, 1991

INVENTOR(S) : CALLINGHAM et al

It is certified that error appears in the above-identified patent and that said Letters Patent is hereby corrected as shown below:

Akers et al, J. Bacteriol. (1980), 141, 164-168, "Thujaplicins from Thuja plicata as Iron Transport Agents for Salmonella typhimurium"

Bothwell et al, Amer. J. Cli. Nutr. (1964), 14, 47-51, "Iron Overload in Bantu Subjects"

Gerard et al, J. Chem. Research (M), (1980), paper F/016/80, 3919-3927.

Signed and Sealed this

Tenth Day of March, 1992

Attest:

HARRY F. MANBECK, JR.

*Attesting Officer*    *Commissioner of Patents and Trademarks*